US011185667B2

(12) United States Patent
Chu et al.

(10) Patent No.: US 11,185,667 B2
(45) Date of Patent: Nov. 30, 2021

(54) MEDICAL DEVICE HANDLE AND METHOD OF USE

(71) Applicant: BOSTON SCIENTIFIC SCIMED, INC., Maple Grove, MN (US)

(72) Inventors: Michael S. H. Chu, Brookline, MA (US); Ashley Taylor, Harrisburg, PA (US); Brian P. Watschke, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 293 days.

(21) Appl. No.: 16/406,577

(22) Filed: May 8, 2019

(65) Prior Publication Data
US 2020/0023163 A1    Jan. 23, 2020

Related U.S. Application Data

(60) Provisional application No. 62/700,634, filed on Jul. 19, 2018.

(51) Int. Cl.
*A61M 25/01* (2006.01)
*A61B 17/22* (2006.01)
(Continued)

(52) U.S. Cl.
CPC ......... *A61M 25/0136* (2013.01); *A61B 10/06* (2013.01); *A61B 17/22031* (2013.01);
(Continued)

(58) Field of Classification Search
CPC ............ A61B 17/2841; A61B 17/2909; A61B 2017/00367; A61B 17/22031;
(Continued)

(56) References Cited

U.S. PATENT DOCUMENTS 5,827,323 A * 10/1998 Klieman ............ A61B 17/2909
606/205
2004/0215212 A1* 10/2004 Teague ................. A61B 17/221
606/127
(Continued)

FOREIGN PATENT DOCUMENTS

WO    WO-2019109060 A1 *  6/2019    ........... A61B 17/221

*Primary Examiner* — Kathleen S Holwerda
*Assistant Examiner* — Uyen N Vo
(74) *Attorney, Agent, or Firm* — Fay Kaplun & Marcin, LLP

(57) ABSTRACT

A handle assembly includes a drive wire coupled to an expandable end effector, the wire having a diameter of no more than 3 French and a handle cannula receiving the wire therethrough, rotation of the handle cannula transferring torque to rotate the wire. The assembly also includes a shaft receiving the handle cannula, rotation of the shaft transferring torque to rotate the handle cannula. The assembly further includes an actuation assembly receiving the shaft, the actuation assembly coupled to a sheath sized to receive the wire and end effector therethrough, the actuation assembly moveable between a proximal configuration in which the sheath is moved proximally to expand the end effector and a distal configuration in which the sheath is moved distally to retract the end effector, the actuation assembly including a rotation mechanism transferring torque to the shaft to rotate the shaft.

6 Claims, 8 Drawing Sheets

(51) Int. Cl.
  *A61B 10/06* (2006.01)
  *A61B 17/29* (2006.01)
  *A61B 17/221* (2006.01)
  *A61B 17/00* (2006.01)

(52) U.S. Cl.
  CPC ... *A61B 17/221* (2013.01); *A61B 2017/00367* (2013.01); *A61B 2017/22035* (2013.01); *A61B 2017/2932* (2013.01)

(58) Field of Classification Search
  CPC ............ A61B 10/06; A61B 2017/2932; A61B 2017/22035; A61B 2018/141; A61B 18/1206; A61B 2018/1253; A61B 18/1492; A61B 2018/00595; A61B 2018/00601; A61B 17/32056; A61B 17/221; A61B 2017/2929
  See application file for complete search history.

(56) References Cited

U.S. PATENT DOCUMENTS

2015/0327878 A1* 11/2015 Chu ..................... A61B 17/221
                                                            606/127
2017/0143980 A1* 5/2017 Soltis ................. A61B 17/3468

* cited by examiner

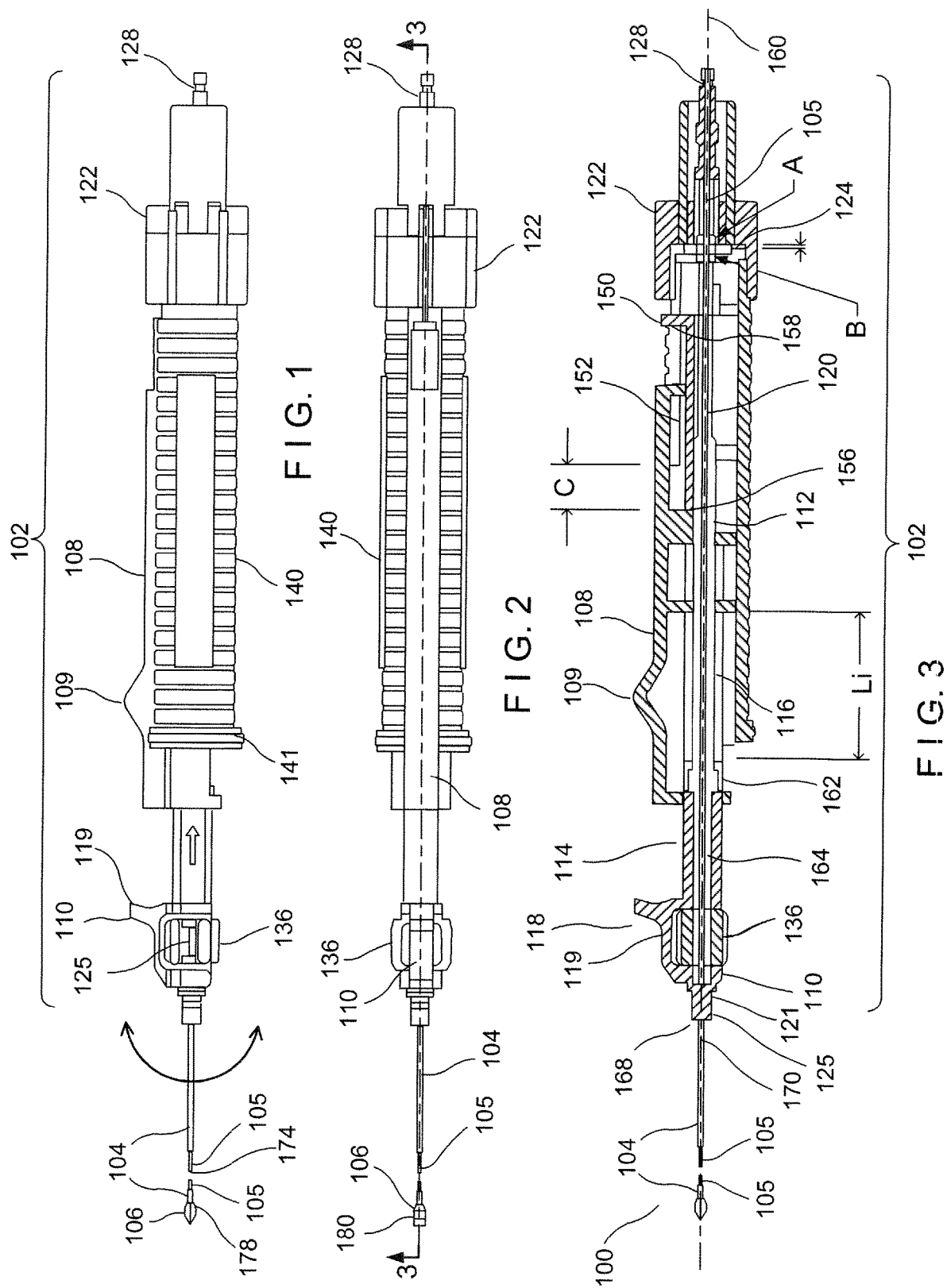

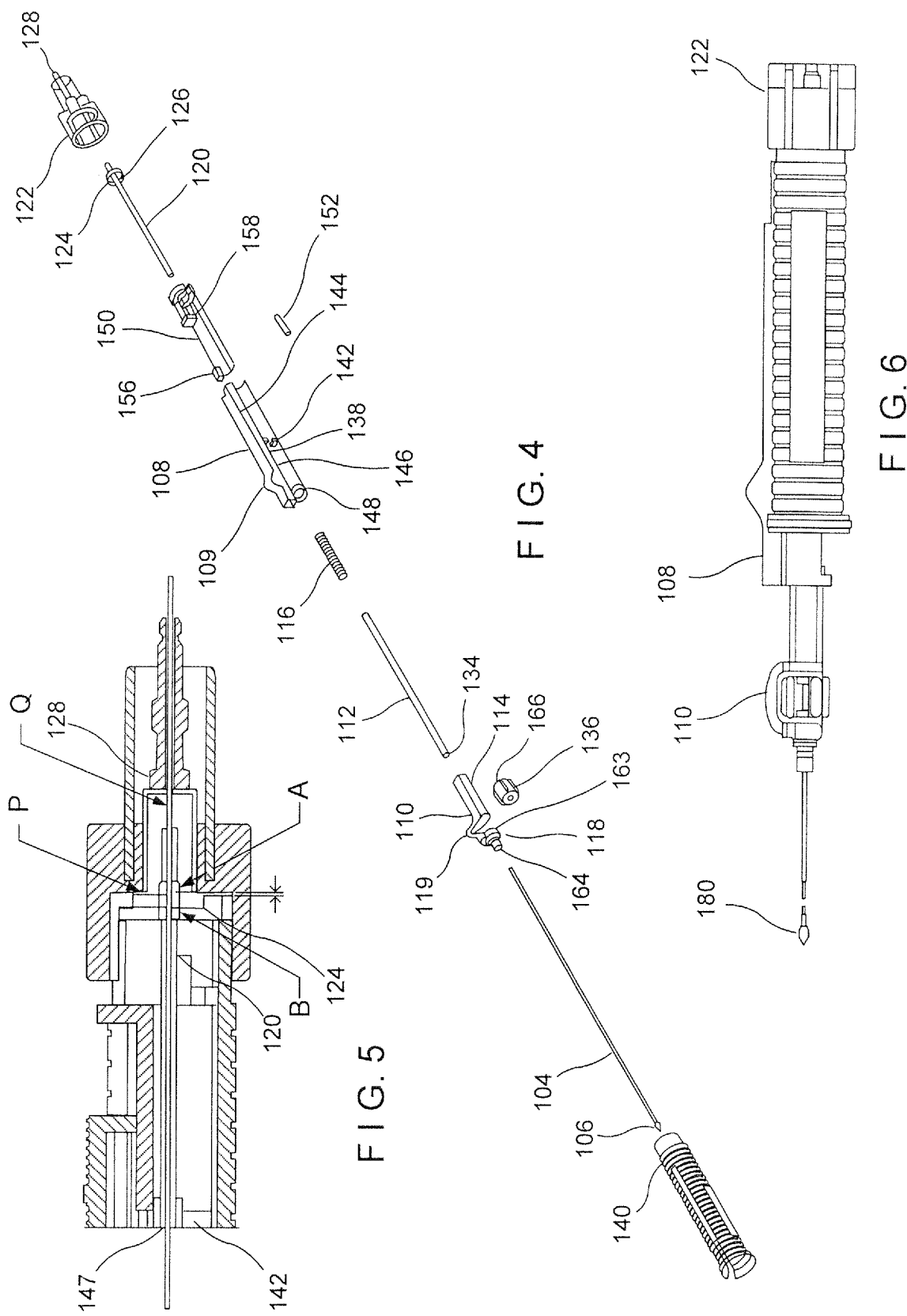

MEDICAL DEVICE HANDLE AND METHOD OF USE

PRIORITY CLAIM

This present disclosure claims priority to U.S. Provisional Patent Application Ser. No. 62/700,634 filed Jul. 19, 2018; the disclosure of which is incorporated herewith by reference.

FIELD

The present disclosure relates generally to retrieval devices and related systems and methods. More specifically, the present disclosure relates to devices, systems and methods for retrieving objects from within a patient's body.

BACKGROUND

Retrieval devices are often used to extract undesired and/or foreign material from the body. In urology, for example, a retrieval device may be used to retrieve kidney and ureteral stones as well as to biopsy tissue from the kidney and ureter through a ureteroscope. Often a flexible ureteroscope with a smaller working channel is used. This smaller shaft limits the outer diameter of the shaft of the retrieval device and the end effector. Current retrieval devices are generally not designed for performing biopsies and often include fragile end effectors that can be easily damaged when used with excessive closure force. Thus, such retrieval devices can biopsy only a small amount of tissue by opening and closing the end effector against the targeted tissue. This motion forces most of the tissue out of the end effector as the end effector is closed to shear off tissue. Less space in the collapsed or closed end effectors allows for minimal prolapsed tissue to remain. Often the end effector is not sharp enough to cut tissue cleanly and the closed end effector must be pulled by the shaft to tear off tissue. Other times the closed end effector is rotated by the shaft to shear of tissue. At times, the small sample is insufficient for histopathological evaluation. Furthermore, pulling or rotating the tissue sample can cause bleeding and another device such as an electrosurgical device may be necessary to cauterize the bleeding tissue or fulgurate the diseased tissue.

SUMMARY

The present embodiments are directed to a handle assembly comprising a drive wire extending from a proximal end to a distal end configured to be coupled to an expandable end effector, the drive wire having a diameter of no more than 3 French and a handle cannula extending from a proximal end to a distal end and configured to receive the drive wire therethrough, the handle cannula including a crimped portion configured to crimp the handle cannula to the drive wire such that rotation of the handle cannula transfers torque to rotate the drive wire, an outer profile of the handle cannula being non-circular in shape in combination with a shaft member extending from a proximal end to a distal end, the shaft member configured to slidably receive the handle cannula therethrough, an inner profile of the shaft member sized and shaped to match the outer profile of the handle cannula such that rotation of the shaft member transfers torque to rotate the handle cannula, an outer profile of the shaft member being non-circular in shape and an actuation assembly configured to slidably receive the shaft member therein, a distal end of the actuation assembly being coupled to a sheath sized and shaped to receive the drive wire and end effector therethrough, the actuation assembly moveable between a proximal configuration in which the sheath is moved proximally to expand the end effector and a distal configuration in which the sheath is moved distally to retract the end effector, the actuation assembly including a rotation mechanism keyed to the outer profile of the shaft member such that rotation of the rotation mechanism transfers torque to rotate the shaft member.

In an embodiment, the actuation assembly includes a first actuation member and a second actuation member, the first actuation member extending from a proximal end to a distal end coupled to the second actuation member, the second actuation member extending from a keyed proximal end to a distal end coupled to the sheath, the second actuation member including the rotation mechanism.

In an embodiment, the first actuation member includes a lumen separated into a proximal portion and a distal portion via a stop rib, the proximal and distal portions being open to one another via a hole in the stop rib sized and shaped to slidably receive the shaft member therethrough, the distal portion being open to a distal aperture configured to receive the keyed proximal end of the second actuation member.

In an embodiment, the handle assembly further includes a locator body extending from a proximal end to a distal end configured to be received within the proximal portion of the first actuation member lumen, the locator body including a lumen sized and shaped to receive the handle cannula, a distal stop for limiting the distal sliding distance of the first actuator, and a proximal stop limiting the proximal sliding distance of the first actuator.

In an embodiment, the second actuation member includes a proximal plunger portion and a distal trigger portion, the plunger portion being keyed to the distal aperture of the first actuation member so as to allow slidable movement of the plunger within the proximal lumen portion of the first actuation mechanism, the trigger portion extending distally from the plunger portion and including a slot to receive the rotation mechanism, the trigger portion configured to be gripped by a user to move the second actuation member proximally and distally relative to the first actuation member to further expand and retract, respectively, the end effector.

In an embodiment, the rotation mechanism is a knob including a channel extending therethrough sized and shaped to receive the shaft, an inner profile of the channel keyed to the outer profile of the shaft.

In an embodiment, the handle assembly further includes a biasing member configured to be positioned over a portion of the shaft within the proximal portion of the first actuator lumen so as to be compressible between the plunger portion and the stop rib, a restoring force of the biasing member being set to less than a break strength of the end effector so that the sheath is distally movable over the end effector when a target tissue is captured therein.

In an embodiment, the handle assembly further includes an end cap with a monopolar plug, the monopolar plug configured to positively complete an energy circuit to the end effector when the actuation assembly is in the proximal configuration.

The present embodiments are also directed to a retrieval device including an end effector moveable between a retracted configuration and an expanded configuration, the end effector having a diameter of less than 3 French, a drive wire extending from a proximal end to a distal end configured to be coupled to an expandable end effector, a handle cannula extending from a proximal end to a distal end and configured to receive the drive wire therethrough, the handle cannula including a crimped portion configured to crimp the handle cannula to the drive wire such that rotation of the handle cannula transfers torque to rotate the drive wire, an outer profile of the handle cannula being non-circular in shape, and an actuation assembly configured to slidably receive the shaft member therein, a distal end of the actuation assembly being coupled to a sheath sized and shaped to receive the drive wire and end effector therethrough, the actuation assembly moveable between a proximal configuration in which the sheath is moved proximally to expand the end effector and a distal configuration in which the sheath is moved distally to retract the end effector, the actuation assembly including a rotation mechanism keyed to the outer profile of the handle cannula such that rotation of the rotation mechanism transfers torque to rotate the handle cannula.

In an embodiment, the actuation assembly includes a first actuation member and a second actuation member, the first actuation member extending from a proximal end to a distal end coupled to the second actuation member, the second actuation member extending from a keyed proximal end to a distal end coupled to the sheath, the second actuation member including the rotation mechanism.

In an embodiment, the first actuation member includes a lumen separated into a proximal portion and a distal portion via a stop rib, the proximal and distal portions being open to one another via a hole in the stop rib sized and shaped to slidably receive the handle cannula therethrough, the distal portion being open to a distal aperture configured to receive the keyed proximal end of the second actuation member.

In an embodiment, the device further includes a locator body extending from a proximal end to a distal end configured to be received within the proximal portion of the first actuation member lumen, the locator body including a lumen sized and shaped to receive the handle cannula, a distal stop for limiting the distal sliding distance of the first actuator, and a proximal stop limiting the proximal sliding distance of the first actuator.

In an embodiment, the second actuation member includes a proximal plunger portion and a distal trigger portion, the plunger portion being keyed to the distal aperture of the first actuation member so as to allow slidable movement of the plunger within the proximal lumen portion of the first actuation mechanism, the trigger portion extending distally from the plunger portion and including a slot to receive the rotation mechanism, the trigger portion configured to be gripped by a user to move the second actuation member proximally and distally relative to the first actuation member to further expand and retract, respectively, the end effector.

In an embodiment, the rotation mechanism is a knob including a channel extending therethrough sized and shaped to receive the handle cannula, an inner profile of the channel keyed to the outer profile of the handle cannula.

In an embodiment, the device further includes biasing member configured to be positioned over a portion of the handle cannula within the proximal portion of the first actuator lumen so as to be compressible between the plunger portion and the stop rib, a restoring force of the biasing member being set to less than a break strength of the end effector so that the sheath is distally movable over the end effector when a target tissue is captured therein.

The present embodiments are also directed to a method for retrieving tissue including inserting a distal portion of a tissue retrieval device to a target area within a living body, the distal portion including an end effector moveable between a retracted configuration and an expanded configuration, the end effector having a diameter of less than 3 French, a drive wire extending from a proximal end to a distal end configured to be coupled to an expandable end effector, a handle cannula extending from a proximal end to a distal end and configured to receive the drive wire therethrough, the handle cannula including a crimped portion configured to crimp the handle cannula to the drive wire such that rotation of the handle cannula transfers torque to rotate the drive wire, an outer profile of the handle cannula being non-circular in shape, and an actuation assembly configured to slidably receive the shaft member therein, a distal end of the actuation assembly being coupled to a sheath sized and shaped to receive the drive wire and end effector therethrough, the actuation assembly moveable between a proximal configuration in which the sheath is moved proximally to uncover and expand the end effector and a distal configuration in which the sheath is moved distally to cover and retract the end effector, the actuation assembly including a rotation mechanism keyed to the outer profile of the handle cannula such that rotation of the rotation mechanism transfers torque to rotate the handle cannula, moving the actuation assembly proximally to uncover the end effector, allowing the end effector to move from the retracted configuration to the expanded configuration, capturing tissue, via the end effector, and retracting the end effector by moving the actuation assembly distally to cover the end effector.

In an embodiment, the method further includes rotating the end effector via the rotation mechanism to position a cutting surface of the end effector against the target tissue.

In an embodiment, the method further includes turning on an electrical generator coupled to an end cap of the tissue retrieval device to allow an electrical current to pass through the tissue retrieval device to the end effector, the end cap including a monopolar plug configured to positively complete an energy circuit to the end effector when the actuation assembly is in the proximal configuration.

In an embodiment, the end effector is configured as an expandable snare including at least one filament, the electrical generator supplying electrical energy to the at least one filament to cut the target tissue.

BRIEF DESCRIPTION

FIG. 1 shows a side view of a retrieval device according to a first exemplary embodiment of the present disclosure;

FIG. 2 shows a top view of the retrieval device of FIG. 1;

FIG. 3 shows a cross-sectional view of the retrieval device of FIG. 1;

FIG. 4 shows a sectional assembly partially exploded view of the retrieval device of FIG. 1;

FIG. 5 shows a cross-sectional view of the proximal end of the retrieval device of FIG. 1 according to an exemplary embodiment of the present disclosure;

FIG. 6 shows a perspective view of a retrieval device according to a second exemplary embodiment of the present disclosure;

DETAILED DESCRIPTION

Figure 7:
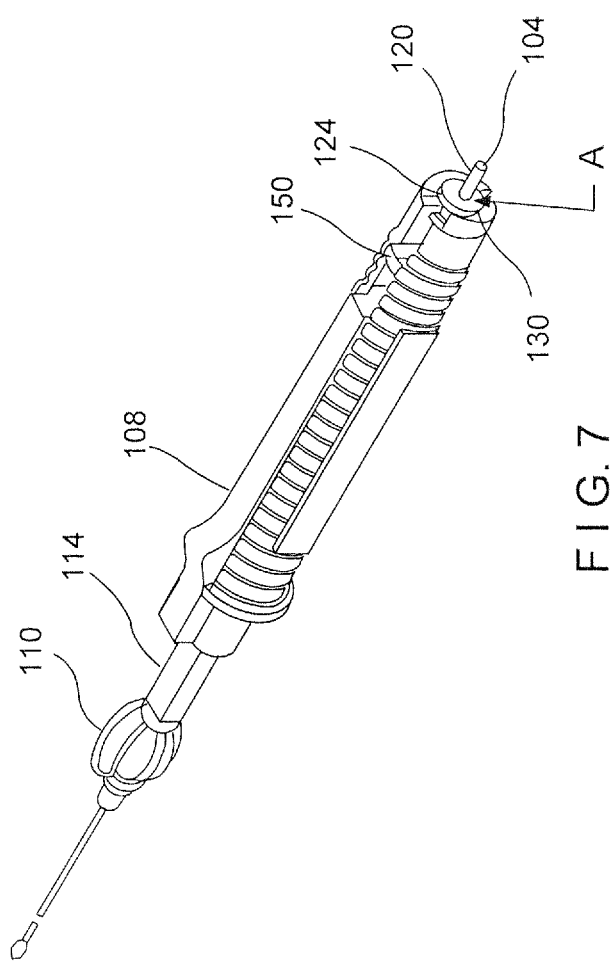
FIG. 7 shows a perspective view of the retrieval device of FIG. 1.
Figure 8:
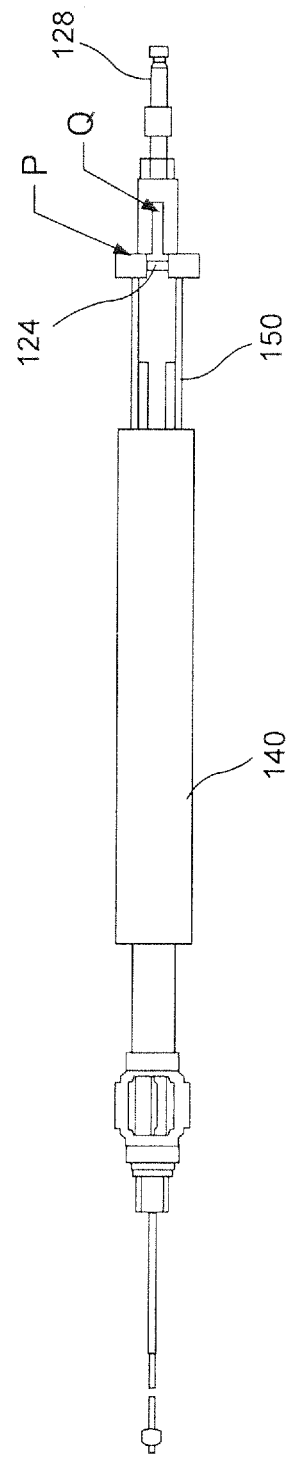
FIG. 8 shows a top, partial cross-sectional view of the retrieval device of FIG. 1 with the end cap removed.
Figure 9:
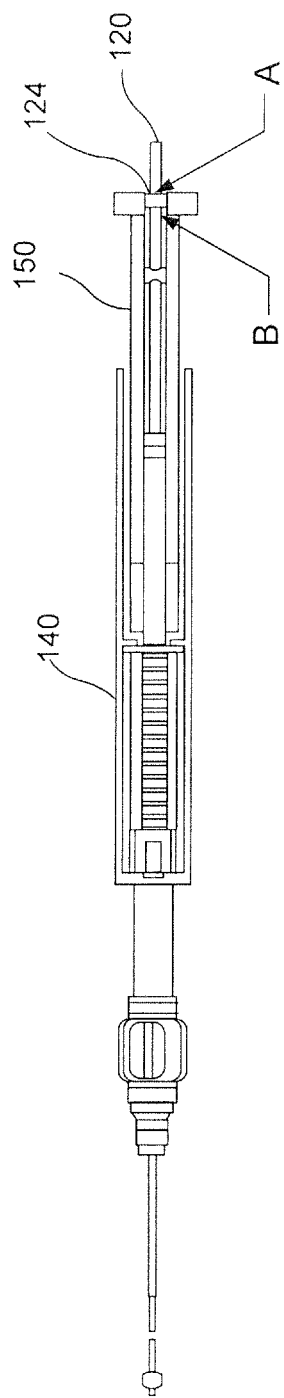
FIG. 9 shows a bottom partial cross-sectional view of the retrieval device of FIG. 1.

The present disclosure may be further understood with reference to the appended drawings and the following description, wherein like elements are referred to with the same reference numerals. The present disclosure relates to retrieval devices and methods for retrieving tissue within a living body. Specifically, the present disclosure relates to a retrieval handle that may be used with a sheath, a drive wire, and an end effector, each having a small diameter (i.e., under 3 French), to achieve a larger biopsy volume. In some embodiments, the drive wire is partially covered by the sheath with the self-expanding end effector attached to the distal end of the drive wire. In other embodiments, non-self-opening end effectors are also attached, associated or "held" by the distal end of the sheath such that the reciprocal motion of the sheath will force the end effector to open and close. In an exemplary embodiment, the retrieval device includes monopolar electrosurgery modalities to all for electrosurgical cutting of the tissue. It should be noted that the terms "proximal" and "distal", as used herein, are intended to refer to a direction toward (proximal) and away from (distal) a user of the device (e.g. physician).

Referring to FIGS. 1-9, a retrieval device 100 includes a handle assembly 102 at the proximal end of the device 100, a sheath member 104, a drive wire 105 and an end effector 106 at the distal end of the device 100. The handle assembly 102 of this embodiment includes a handle body 140, a first actuator or actuation member 108, and a second actuator 110. As shown in FIG. 3, the second actuator 110 in this embodiment is formed as a trigger assembly and includes various components, such as a shaft 112, a plunger 114, a biasing member 116 and a trigger assembly 118. The second actuator 110 is configured to reciprocate within the first actuator 108. As will be discussed in further detail below, the first actuator controls the opening and closing of the end effector via a spring and the movement of the drive wire 105 while the second actuator overrides the restoring spring force to further retract or extend the sheath. It should be noted that the trigger assembly 118 can be used to further close the end effector when the spring restoring force is of insufficient strength to close the end effector.

The handle assembly 102 also includes a handle cannula 120 extending therethrough from an end cap 122 at a proximal end of the retrieval device 100. The handle cannula 120, in this embodiment, is preferably formed of brass or stainless steel and has a polygonal outer profile extending along its entire length or a partial length thereof to facilitate the application of torque thereto to rotate the drive wire 105.

In this exemplary embodiment, the handle cannula 120 has a square outer profile. However, it will be understood by those skilled in the art that the handle cannula 120 may have any other suitable non-circular outer profile, such as an oval profile, so long as the handle cannula 120 is capable of transferring torque to a drive wire 105 received therein. In an exemplary embodiment, an inner profile of the handle cannula 120 is circular. However, it is understood that the inner profile may be any suitable shape. The handle assembly 102 further includes a metal washer 124 slidably positioned over the handle cannula 120. The washer 124 includes a hole 126 extending therethrough, an internal diameter of the hole 126 of the washer 124 being sized and shaped to allow rotation of the handle cannula 120 therein without contact between the handle cannula 120 and the washer 124. As will be explained in further detail below, this clearance between the handle cannula 120 and the washer 124 creates an interruption in the circuit from an active plug 128 at a proximal end of the device 100 to the end effector 106 at the distal end of the device 100. The washer 124 is sized and shaped to be positioned within a U-recess 130 of the handle body 140 and cap 122, as shown in FIG. 7. The handle cannula 120 may be crimped on both sides of the washer 124 at points A and B, shown in FIGS. 5 and 9, to prevent the washer 124 from migrating along the handle cannula 120 and to prevent the handle cannula 120 from migrating within the handle relative to the washer 124 and cap 122. The crimps A, B also secure the handle cannula 120 to the drive wire 105 such that rotation of the handle cannula 120 transfers torque to also rotate the drive wire 105 and the attached end effector 106 at a distal end 178 of the drive wire 105, as further detailed below.

A shaft member 112 extends through the handle assembly 102 and includes a longitudinally-extending lumen 134 extending therethrough. In an exemplary embodiment, an inner profile of the lumen 134 is equal to or slightly larger than the outer profile of the handle cannula 120 such that the handle cannula 120 may be slidably received within the shaft member 112. An inner profile of the shaft member 112 is shaped to match the outer profile of the handle cannula 120 so that rotation of the shaft member 112 transfers torque therebetween to also rotate the handle cannula 120 therein. The shaft member 112 may have any desired non-circular outer profile such as, for example, oval, polygonal, etc. As will be explained in more detail below, the shaft member 112 is received within a knob 136 keyed thereto to such that rotational movement or torque is applied to the knob 136 is transferred to the shaft member 112 and, thus, to the handle cannula 120 therein.

The first actuator 108, in this embodiment, has a generally cylindrical shape including a lumen 138 extending therethrough and is configured to be slidably received within the handle cover 141. As best seen in FIG. 1, the first actuator 108 may have a protrusion 109 its upper surface, against which the user may exert force using his or her thumb to move the first actuator 108 proximally or distally relative to the handle cover 141 to transition the end effector 106 between an expanded configuration and a retracted configuration. The actuation member protrusion 109 extends from a lateral side of the first actuator 108 and is configured to be slidably received within a slot 154 of the handle cover 141. A stop rib 142 is positioned within the lumen 138, separating the lumen 138 into a proximal portion 144 and a distal portion 146. The proximal 144 and distal 146 portions of the lumen 138 are open to one another via a U-shaped opening 147 in the stop rib 142. The hole 147 is sized and shaped to slidably receive the shaft member 112 therethrough. The distal portion 146 of the lumen 138 is also open to a distal aperture 148 which, in this embodiment, includes two flat sides for receiving the keyed proximal end of the plunger 114. The proximal portion 144 of the lumen 138 is configured to receive a locator body 150 and a stroke limiter 152, as will be discussed in further detail below.

The locator body 150 is sized and shaped to be disposed within the proximal portion 144 of the first actuator lumen 138 and, in this embodiment, is operatively coupled to or formed within the handle body 140. The locator body 150 includes a lumen 151 sized and shaped to receive the handle cannula 120. One or more protrusions or stops are positioned along the length of the locator body 150 for controlling the longitudinal movement of the first actuator 108. For example, as shown in FIG. 3, the locator body 150 limits the distal sliding distance of the first actuator via a first distal stop 156 and the proximal sliding distance via a second proximal stop 158. Specifically, when the stroke limiter 152 abuts the distal stop 156, the first actuator 108 is prevented from further distal movement whereas when the proximal end of the first actuator 108 abuts the proximal stop 158, the first actuator 108 is prevented from further proximal movement.

The stroke limiter 152 is also configured to be positioned within the proximal portion 144 of the first actuator 108. The stroke limiter 152 may be a separate component such as a tube or may be formed on the first actuator 108. The stroke limiter 152 is preferably formed of a polymer and has a predetermined length depending on the particular end effector being used. Specifically, the stroke limiter 152 is positioned within the proximal portion 144 of the first actuator 108 and governs the distance the first actuator 108 can move in the distal direction. As can be seen in FIG. 3, the distance the first actuator 108 is able to move distally is determined by the distance between a distal face of the stroke limiter 152 and a proximal face of the distal stop 158 of the locator body 150.

The end cap 122 is coupled to the proximal end of the handle body 140 and includes an active plug 128. The end cap 122 may be coupled to the handle body 140 in any suitable manner (e.g., fasteners, adhesives, molding). For example, in an exemplary embodiment, the handle body 140 may include an externally threaded portion and the end cap 122 may include a complementary internal threading so that the end cap 122 may be screwed onto the handle assembly 102. The end cap 122, in this embodiment, is composed of any suitable polymer for example, for insulation, while the plug 128 is composed of brass or any other suitable metal for example, to conduct an electric current. The plug 128 may be coupled to the end cap 122 via, for example, adhesive or screw threading. The plug 128 is configured for coupling to for example, an energy generator. In an exemplary embodiment, the plug 128 is coupled to the energy generator via a lead 160. The energy generator may supply any suitable energy such as electrical, laser, thermal, ultrasound, etc. The lead 160 and plug 128 may have any suitable size shape and geometry and may be manufactured using any suitable materials providing insulation on the exterior of the lead 160 and the plug 128. In an alternate embodiment shown in FIG. 6, the end cap 122 does not include an active plug. Thus, in this embodiment, the device 100 does not include the energy modality described above.

The second actuator, or trigger assembly 110, includes a proximal plunger portion 114, a distal trigger portion 118 and a channel 164 extending therethrough. The plunger portion 114, in this embodiment, is formed with flat lateral sides keyed to the distal aperture of the first actuator 108 to allow slidable movement of the plunger 114 within the proximal lumen portion 144 of the first actuator 108 while preventing rotation of the plunger. The trigger assembly 110 may be operatively coupled to the first actuator 108 in any suitable manner. For example, as shown in FIG. 3, the trigger assembly 110 may include flexing tabs 162 which engage an interior surface of the first actuator 108. The flexing tabs 162, in an exemplary embodiment, are formed on the outer surface of the plunger 114 and snap into corresponding slots on the inner surface of the lumen of the first actuator 108. In other embodiments, the flexing tabs 162 may be replaced by keyed tabs, fasteners, screws, or any other suitable couplings that allow limited two-way movement of the plunger 114 relative to the first actuator 108. The trigger portion 118 of the trigger assembly 110 extends distally from the plunger portion 114 to a distal tip 121 and includes a trigger 119 and a slot 163 to receive a knob 136. The knob 136 has a channel 166 extending therethrough and open to the trigger assembly channel 164 to receive the shaft 112. The channel 166 has an inner profile that, as noted above, is keyed to the non-circular outer profile of the shaft 112 extending therethrough to translate torque from the knob 136 to the shaft 112. In an exemplary embodiment, the shaft 112 may be glued to the knob 136 via a glue slot 125 to transfer torque as well as to prevent migration of the shaft 112 in the channel 166 of the knob 136. The distal tip 121 of the trigger assembly 110 may be fixedly coupled to a proximal portion of the sheath 104 in any suitable manner such as via fasteners, snap fasteners, insert molding, heat shrink, adhesive, weld, etc. In an example, the trigger assembly 110 may be insert molded on the sheath 104. The sheath 104 terminates just proximal to the distal tip 121 while the drive wire extends proximally in the lumen of the shaft member 112 through the channel of the trigger assembly 110 and the lumen 138 of the first actuator 108 and, in this embodiment, is operatively coupled to the handle assembly 102 at the end cap 122. Any suitable materials or combination of materials having any suitable properties may be used to form the components of the handle assembly 102 such as, for example, metals or polymers. The plunger 114 and the shaft 112 may have any suitable size and shape. For example, the plunger 114 may have flat, planar exterior surface for keyed coupling with the first actuator 108 and the shaft 112 may have a round tubular shape over which the biasing member 116 may be disposed.

The biasing member 116, in this embodiment, is a compression spring that, as would be understood by those skilled in the art, substantially obeys Hook's law and is formed of stainless steel or any other suitable metal. The biasing member 116 is configured to be positioned over a portion of the shaft 112 in the distal portion 146 of the first actuator lumen 138 so as to be compressible between the plunger 114 and the stop rib 142 of the first actuator 108. The biasing member 116 has an initial resting length, or initial height, $L_i$, depicted in FIG. 3, with an initial force of the spring at the initial height $L_i$ being $F_1$. As one skilled in the art would understand, the resting length of the spring is when the spring is at its free or equilibrium length where it has not been compressed or tensioned. As will be discussed in further detail below, the restoring force of the compressed spring can be calculated using Hook's law.

The sheath 104 of the device 100 extends from a proximal end 170 to a distal end 172 and includes a longitudinally-extending lumen 174. The proximal end 170 is coupled to the distal end of the trigger assembly 110. The sheath 104 may be, for example, a hollow tube and may be manufactured using any suitable material or combination of materials, depending on the configuration of the device 100. For example, a retrieval device 100 with an electrosurgical modality according to an exemplary embodiment that is configured to transmit an electric current through the drive wire 105 may have a sheath 104 composed of an insulative polymer to insulate the current from the user as well as the patient. However, if the device 100 does not include an electrosurgical modality, the sheath 104 may be composed of any other suitable material such as, for example, metals, braided metals, etc. In further embodiments, the conductive metal in the sheath can be sandwiched between insulation and can be used as a return path for, i.e., a bipolar device. The sheath 104 may have any suitable features such as, for example, varying flexibility, therapeutic coatings, visualization features (for direct visualization and/or viewing by an imaging device), surface features (e.g., protrusions, indentations, roughened portions), shape memory properties, etc. The sheath 104, in this embodiment, has a diameter that is 3 French or less so as to be able to navigate a tortuous path to the kidney within the working channel of a ureteroscope. However, it will be understood that the sheath 104 may have any suitable size and shape depending on the procedure or application of the device 100. A length of the sheath 104 is selected to matched to a length of the drive wire 105. In an embodiment, portions of the sheath 104 may be covered by various materials such as coatings and/or covers having various suitable properties.

The drive wire 105 extends longitudinally from a proximal end 176 to a distal end 178. The distal end 178 is coupled to the end effector 106 while the proximal end 176 extends proximally through the retrieval device 100 to a proximal portion of the handle cannula 120 to create an energy line to the end effector 106, as will be described in further detail below. The drive wire 105 may be formed from, for example, Stainless steel, nitinol or any other suitable metal so as to create an electrical path from the handle assembly 102 to the end effector 106.

The end effector 106, in an exemplary embodiment, is configured as an expandable snare. However, it will be understood that any end effector may be used, so long as the end effector is operated using reciprocal motion. The end effector 106, as previously noted, in this embodiment, is moveable between a retracted and an expanded configuration, the expanded configuration shown in FIGS. 1-8. In the present exemplary embodiment, the end effector 106 comprises a single filament 180 extending from a first end to a second end, the filament 180 forming the snare. The first and second ends may be coupled to the drive wire 105 such that electrical energy may be provided to the expandable snare 106 through the device 100. In an embodiment, some portions of the filament 180 forming the expandable snare 106 may be insulated using an electrical insulator so they do not transmit energy to undesirable areas of the operating field. In another exemplary embodiment, the end effector 106 may take the form of an expandable basket including multiple filaments 180. In this embodiment, one of the filaments 180 may be electrically coupled to the energy source while the other filaments are insulated from the electrical current. As would be understood by those skilled in the art, this electrosurgical device may be formed as a monopolar device with an external return pad to complete the circuit or as a bi-polar device where both electrodes are formed on internal components of the device itself.

Figure 17:
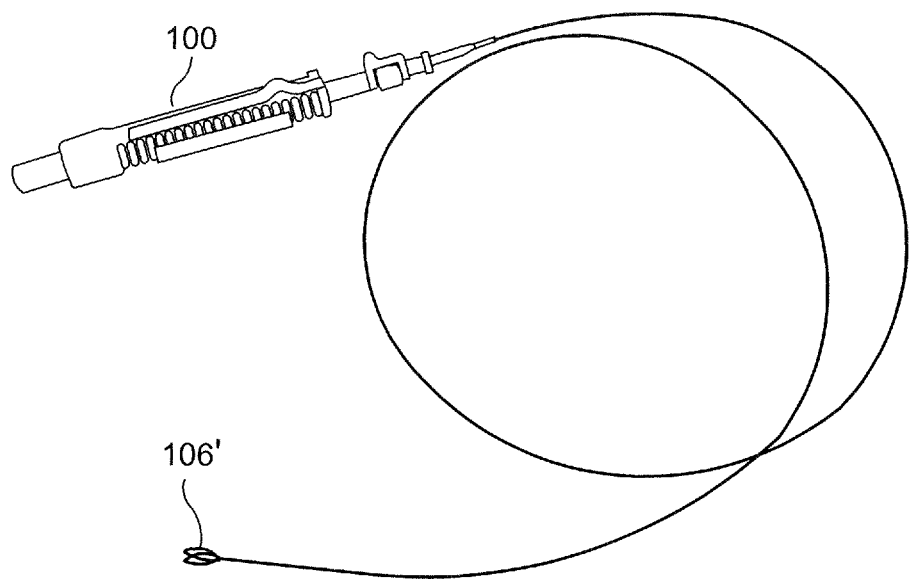
FIG. 17 shows an end effector according to an exemplary embodiment of the present disclosure.

In another exemplary embodiment depicted in FIG. 17, the device 100 may include a Graspit™ end effector 106'. The Graspit™ end effector 106' is a self-expanding end effector that springs open when expanded from the sheath 104. The Graspit™ end effector 106' includes nitinol forceps designed for secure grasp and release of stones within the body. A serrated wire edge is used to provide enhanced holding power for a more secure manipulation and more reliable stone retrieval. The Graspit™ end effectors may be 8 mm or 10 mm in size and accommodate a range of stone sizes. Furthermore, the flexible nitinol construction is designed to reduce impact on scope deflection.

Figure 10:
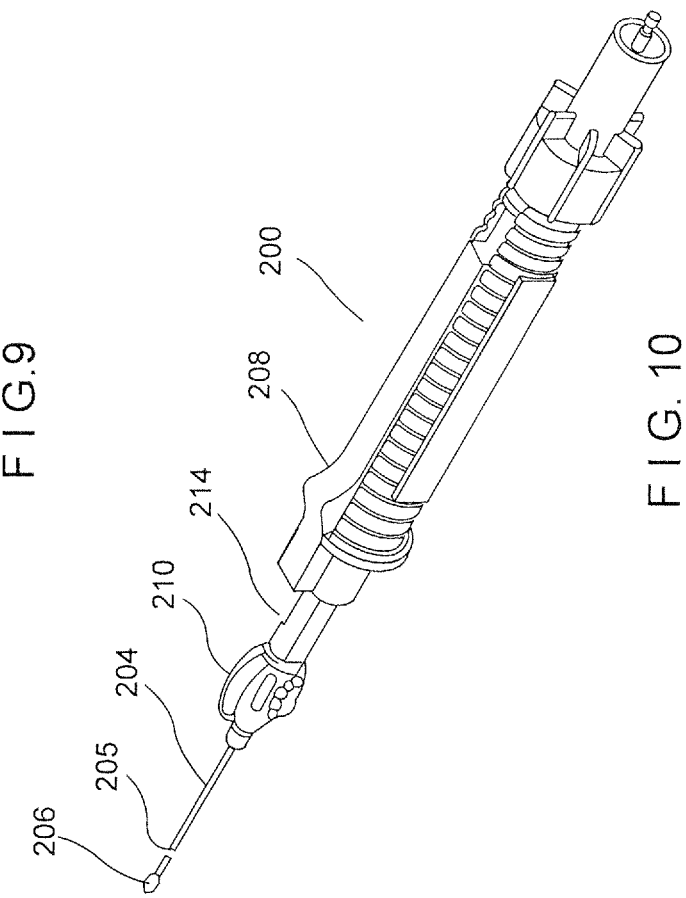
FIG. 10 shows a perspective view of a retrieval device according to a third exemplary embodiment of the present disclosure.

The internal components of the handle assembly 102 may be assembled by inserting the knob 136 into the slot 163 of the trigger assembly 110. The shaft member 112 is then inserted through the proximal end of the plunger 114 and through the channel 166 of knob 163. The distal end of the shaft member 112 may rest in the channel 166 just distal to the knob 163 such that the knob 163 is supported at both sides by the shaft member 112. The biasing member 116 is positioned on the shaft 112 and the trigger assembly 110 is inserted into the keyed distal aperture 148 of the first actuator 108. The flexing tabs 162 of the trigger assembly 110 are inserted through the keyed distal aperture 148 and snap into place within the first actuator 108. This insertion compresses the biasing member 116 against the stop rib 142 to its initial compressed length Li with the biasing member's 116 restoring force extending the moveable plunger 114 in the distal direction. The knob 163, in this embodiment, is glued to the shaft member 112 via the glue slot 125 or coupled to the shaft member 112 via a press fit or by mechanical lock as would be understood by those skilled in the art. The sheath 104 and the drive wire 105 are loaded into the assembled trigger assembly 110 and the proximal end of the sheath 104, in an exemplary embodiment, is glued directly to the distal end 168 of the trigger assembly 110. In another embodiment, the sheath 104 may be coupled to the distal end 168 of the trigger assembly 110 via a hub connection. The stroke limiter 152, having a predetermined length for a particular size end effector 106, is positioned in the proximal portion 144 of the first actuator lumen 138 and the locator block 150 is placed into the proximal portion 144 such that the distal stop 158 of the locator block 150 is located distally of the stroke limiter 152. The handle cannula 120 is inserted over the drive wire 105, through the proximal end of the locator block 150, and into the inner profile of the shaft 112. At this point, the washer 124 can be slid onto the handle cannula 120 and positioned into the U-recess 130 of the end cap 122. The drive wire 105 is adjusted at the proximal end of the handle cannula 120 to position the end effector 106 within the sheath 104 in a closed retracted configuration while the first actuator 108 is in the distal closed position. In this closed position, the distance C between the stroke limiter 152 and the first stop 156 is equal to 0. The handle cannula 120 is then crimped on both sides of the washer 124 at points A and B to set the closed configuration of the end effector 106 to the distal first actuator 108 position. FIG. 10 illustrates a bottom view of the handle assembly 102 where a crimper can access the handle cannula 120 through the openings of locator body 150 to create crimps A, B on either side of the washer 124. The crimps A, B also secure the handle cannula 120 to the drive wire 105 such that rotation of the knob 136 transfers the torque via the shaft 112 and the handle cannula 120 to the drive wire 105 and, consequently, to the attached end effector 106. It is noted that rotation of the knob 136 does not rotate the sheath 104, only the shaft 112, handle cannula 120, drive wire 105 and end effector 106. To prevent the drive wire 105 from migration proximally or distally relative to locator body 150, the washer 124 is held, contacted or compressed by the active plug 128 as the end cap 122 is tightened to the screw thread of the handle body 140 which was previously slid to the proximal end of the locator body 150 from a distal end of the first actuator 108.

In an exemplary embodiment, the handle assembly 102 is designed to positively complete an energy circuit as the end effector 106 is closed about the targeted tissue. In this embodiment, when the first actuator 108 is moved distally to close the end effector 106 and capture/cut tissue, the compression force of the sheath 104 on the proximal side of the end effector 106 forces the drive wire 105 to also move in the distal direction. This movement of the drive wire 105 causes the crimp A to be compressed at point P, depicted in FIG. 8, against the washer 124 to complete the circuit to the active plug 128. In another embodiment, the handle cannula 120 or the drive wire 105 may be deflected or bent at point Q, depicted in FIG. 8, to contact the cylindrical wall of the active plug 128 and complete the electrical circuit from the end effector 106 to the active plug 128. In yet another embodiment, a spring may be used to complete the circuit to the active plug 128 while allowing the handle cannula 120 and drive wire 105 to rotate.

As described above, the device 100 may be used to retrieve a target object such as organic material (e.g., kidney stones, ureteral stones, blood clots, tissue to be sampled, etc.) and inorganic material (e.g., components of a medical device or other foreign matter), which may obstruct or otherwise be present within a patient's body cavities or passages. The device 100 may be configured for single hand use while the other hand may be used to manipulate another portion of the device 100 or another device, such as an ureteroscope. In this manner, using the trigger assembly 110 and the first actuator 108, the user may manipulate and maneuver both the device 100 and any other device (e.g., a scope) without the aid of an assistant. The user may use the two actuators—the first actuator 108 and the second actuator or trigger assembly 110 to manipulate the retraction and/or extension of the sheath member 104 relative to the end effector 106 to open and close the end effector 106.

As shown in FIGS. 1-2, the end effector 106 may be opened to capture the target tissue. In order to accomplish this, the actuation member protrusion 109 is gripped and the first actuator 108 moved proximally relative to the handle body 140 along the locator body 150. When moving the actuation member protrusion 109 in the proximal direction, the inner wall of the distal aperture 148 of the first actuator 108 pulls the trigger assembly 110 (via the flexible tabs 162 and the plunger 114) in the proximal direction. This proximal motion of the trigger assembly 110 slides the shaft 112 proximally over the distal end of the handle cannula 120. That is, the distal end of the handle cannula 120 is displaced within the shaft 112 as the first actuation member protrusion 109 is moved proximally. As the first actuator 108 moves proximally, the sheath 104 may withdraw proximally to expose the end effector 106, allowing the self-expanding end effector 106 to open or expand. This proximal movement is accomplished by the abutting connection of the proximal end of the plunger 114 with the first actuator 108 by the flexing tabs 162, and the connection of the distal end of the plunger 114 to the sheath member 104. With the end effector 106 in the expanded configuration, a proximal end of the first actuator 108 may abut the proximal stop 158 of the locator block 150.

The trigger assembly 110 is used to further retract the sheath 104 to uncover the end effector 106 when the first actuator 108 is in its proximal-most configuration. To further retract the sheath, the trigger 119 is actuated to move the trigger assembly 118 in the proximal direction. Specifically, the trigger 119 is operated with the index finger or the thumb to further pull the trigger assembly 118 proximally. This further distal movement and thus, greater expansion of the end effector 106, may be beneficial in instances where, for example, a repositioned or oversized stone is stuck in the end effector 106. Proximal movement of the trigger assembly 118 compresses the biasing member 116 and draws the sheath 104 proximally to further extend or open the end effector 106. Upon release of the trigger 119, the biasing member 116 returns the trigger assembly 118 back to its original distal resting position. The change in the length of the biasing member 116 is equal to the movement of the sheath member 104 relative to the first actuator 108. The trigger assembly 110 may also be moved in the distal direction to further extend the plunger 114 and sheath 104 when the first actuator 108 is in its distal-most position. This distal movement may be beneficial in instances where, for example, the sheath and the drive wire are binding in a tortuous path of the human body or the end effector 106 is capturing a small (i.e., 1 mm) stone when navigating a tortuous path within the human body. It is noted that the length between the proximal end of the shaft 112 and the proximal wall of the locator body 150 is equal to the stroke length of the trigger assembly 110. Thus, the shaft 112 may be cut to any length to increase or decrease the stroke of the trigger assembly 110 to control the maximum end effector open size.

In use, when closing the end effector 106 in air (without a burden) the resistant force of advancing the sheath 104 fully over the end effector 106 is minimal and is less than the initial force F1 of the biasing member 116. Therefore, advancing the actuation member protrusion 109 in the distal direction to retract or cover the end effector 106 will not further compress the biasing member 116. However, when closing the end effector 106 with a burden (such as when the end effector has captured a tissue or a kidney stone), the resistant force of advancing the sheath 104 fully over the burdened end effector 106 can be elevated such that the resistant force is higher than F1. As the actuation member protrusion 109 is moved distally, the burden prevents and restricts further advancement of the sheath 104 over the end effector 106. The trigger assembly 110, which is attached to the sheath 104, is also restricted from further distal movement. As the actuation member protrusion 109 is moved further distally until the distance C between the distal end of the locator body 150 and the proximal face of the stroke limiter 152 reaches zero, the force of the user's hand compresses the biasing member 116 to a second load length $L_2$. The force that is applied to the sheath 104 is a portion of the applied hand force that was applied to the actuation member protrusion 109. The applied force to the sheath 104 when C=0 is the restoring force $F_2$ of the biasing member 116 at $L_2$. As one skilled in the art would understand, $F_2$ is calculable using Hooke's Law.

F2 is also known as the grip force of the end effector 106 when capturing a tissue burden. $F_2$, or the change in length from $L_i$ to $L_2$, is directly proportional to the burden size. To increase the durability of a fragile end effector 106 with a width/diameter of less than 3 French, $F_2$ is set to be less than the break strength of the end effector 106. The largest anticipated burden size is used in calculations for the maximum exerted loads of the biasing member 116. $F_2$ can also be known as the strangulation force of an end effector 106. As the end effector 106 cuts tissue, the sheath 104 extends distally over the end effector 106 due to the restoring force of the biasing member 116. As the end effector 106 cuts, the loop of the filament 180 of the end effector 106 becomes smaller in size as the biasing member 116 becomes longer while $F_2$ becomes smaller in magnitude until the end effector loop is closed and the restoring force returns back to $F_1$ at $L_i$. Thus, the strangulation/cut force is controlled by the restoring force of the biasing member 116, which is consistent for every user. In another embodiment, a light spring may be used as a biasing member to allow the end effector 106 to capture soft tissue, such as soft kidney stones. In this embodiment, the capture force is at a minimum such that the end effector 106 does not crush the soft stone/tissue into multiple pieces. While the first actuator 108 and the trigger assembly 110 are used to open and close the end effector 106, the knob 136 is used to rotate the end effector 106 and the active plug 128 provides an electrical path to the end effector 106. The device 100 can be used conventionally to capture stones and/or biopsy tissue with the added advantage of an electrosurgical device. For example, the exposed tip of the end effector 106 can be used as a cautery pen while the end effector snare filaments 180 may be used as electrosurgical cutting blades.

In an exemplary method according to the present disclosure, the end effector 106 is maintained in the retracted configuration and inserted into the body, e.g., through the working channel of an insertion instrument such as a flexible ureteroscope. Once the end effector 106 has been positioned as desired adjacent to the target tissue, the actuation member protrusion 109 is advanced proximally, moving the trigger assembly 110 and thus, the sheath 104, proximally to uncover the end effector 106, allowing the end effector 106 to move from the retracted configuration to the expanded configuration. If desired, the trigger assembly 110 may be moved proximally to further retract the sheath 104 from the end effector 106, resulting in further expansion of the end effector 106. The end effector 106 may be rotated, via the knob 136, to position the exposed cutting filament 180 against the target tissue. With the end effector 106 in the expanded configuration, a large amount of target tissue is able to prolapse into the end effector 106. The end effector 106 may be rotated again, via the knob 136, forcing the exposed end effector filament 180 into the target tissue. At this point, the electrical generator may be switched on to allow current to pass through the device 100, through the drive wire 150, the exposed filament 180 and back to the return pad or path to cut tissue. Once cut, the tissue drops into the end effector 106 and the end effector 106 is closed by moving the actuation member protrusion 109 in the distal direction. The device 100 is then withdrawn from the body and biopsied tissue removed from the end effector 106 for analysis. The device 100 may be reinserted to use electrosurgical modalities to treat bleeding tissue, etc.

FIGS. 10-14 depict retrieval device designs according to further embodiments of the invention. The retrieval device 200 shown in FIG. 10 is substantially the same as the retrieval device 100 depicted in FIGS. 1-9, except as discussed herein. Regarding FIG. 10, a device 200 is shown with a second actuator 210. However, in this embodiment, the second actuator 210 does not include a trigger. In this embodiment, the knob 236 or the surface of the second actuator 210 may be used instead of the trigger. In an embodiment, the surface of the second actuator 210 or plunger 214 may include ridges or similar characteristics to improve gripability by the user. In this embodiment, the plunger portion 214 of the second actuator 210 may be fixed to the first actuator 208 such that the plunger 214 does not move relative to the first actuator 208. For example, the plunger portion 214 may be glued or molded to the distal end of the first actuator 208. In this embodiment, the device 200 does not include a biasing member because the plunger 214 does not move proximally or distally relative to the first actuator 208. The device 200 still has the single hand operation feature to expand and retract the end effector 206 via the sheath member 204, provide end effector 206 rotation via the knob 236 and provide an electrical current to the end effector 206 via the drive wire 205.

Figure 11:
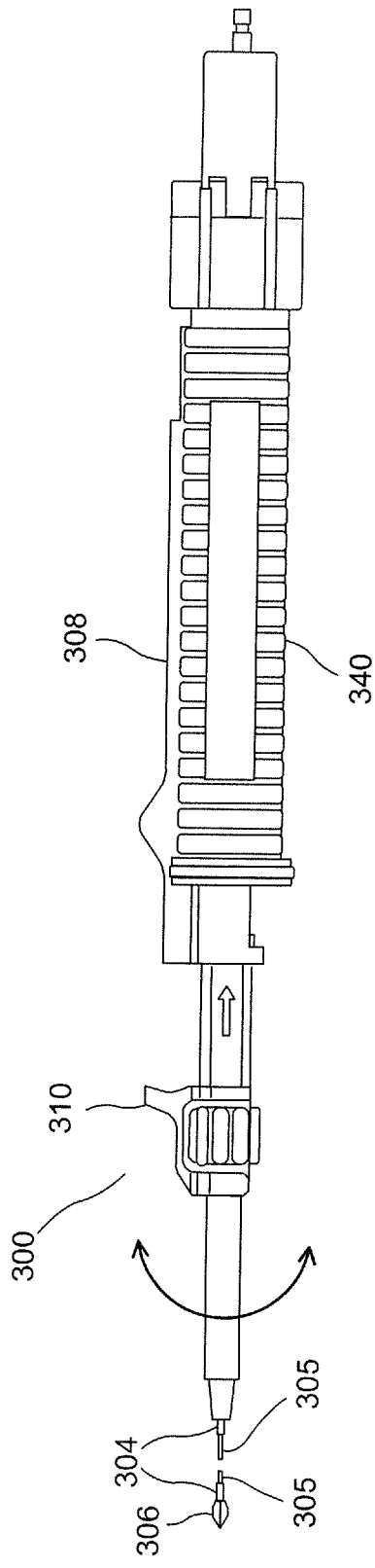
FIG. 11 shows a side view of a retrieval device according to a fourth exemplary embodiment of the present disclosure.
Figure 12:
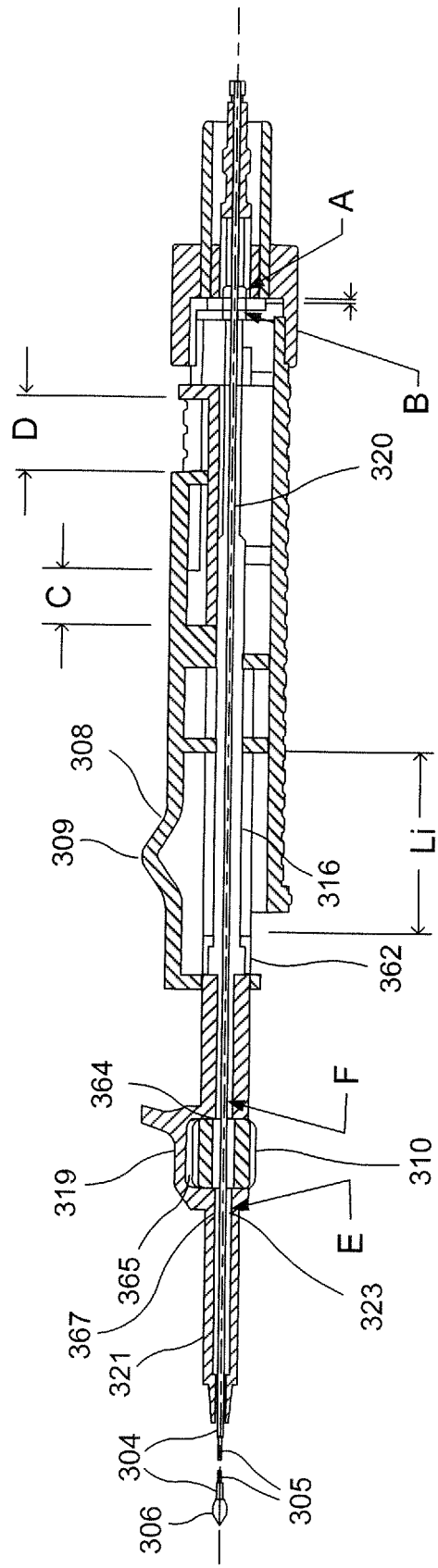
FIG. 12 shows a cross-sectional side view of the device of FIG. 11.
Figure 13:
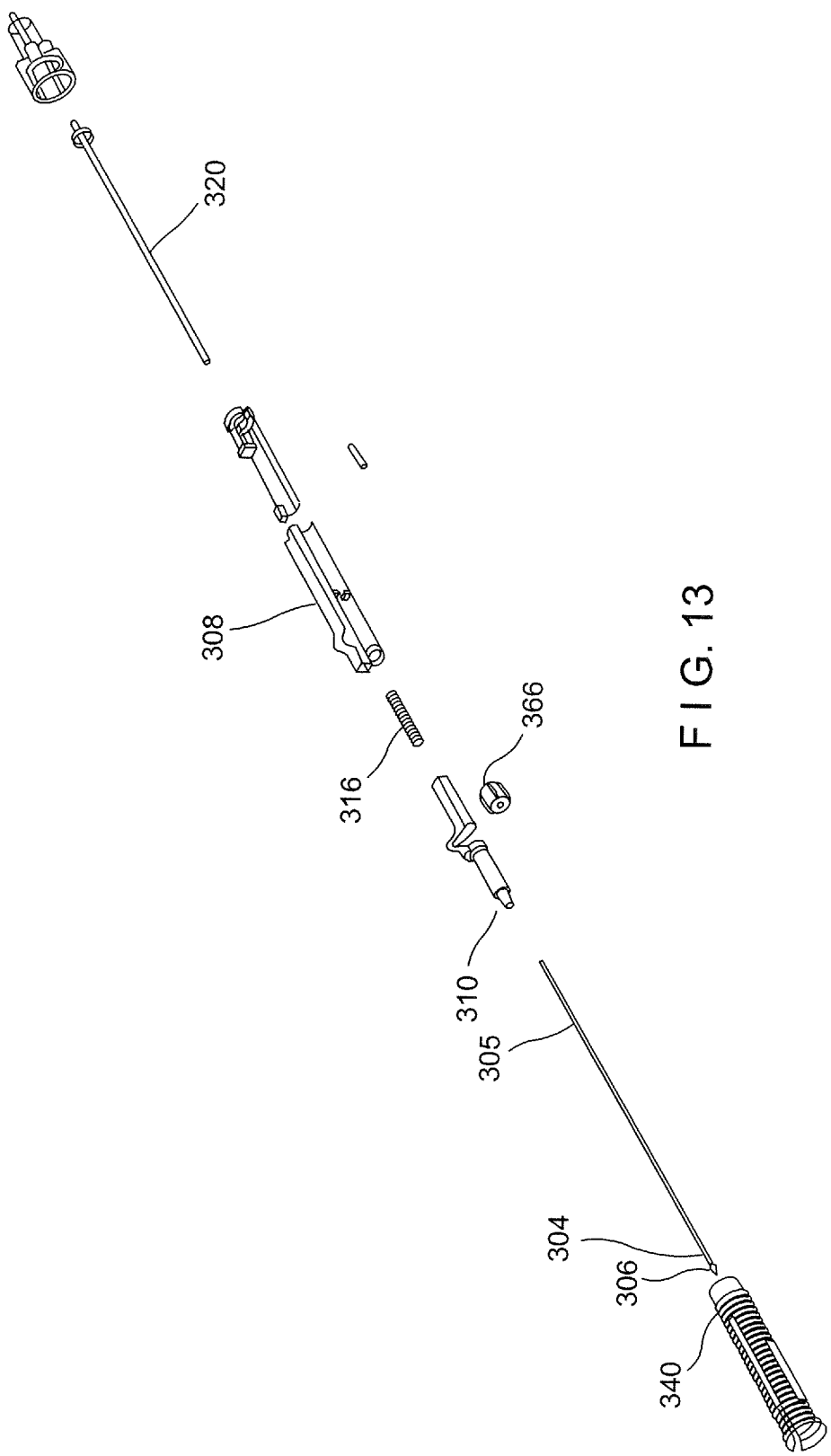
FIG. 13 shows a sectional assembly view of the retrieval device of FIG. 11.

FIGS. 11-13 depict retrieval device designs according to further embodiments of the invention. The retrieval device 300 shown in FIGS. 11-13 are substantially the same as the retrieval device 100 depicted in FIGS. 1-10, except as discussed herein. Specifically, the device 300 includes a first actuator 308, a trigger assembly 310, a handle cannula 320, a biasing member 316, a drive wire 305 and a locator body 350. However, the retrieval device 300 does not include a shaft such that torque is transferred directly from the knob 336 to the handle cannula 320. In this embodiment, the knob 336 may have a channel 366 with a keyed inner profile that is equal to or slightly larger than the outer matching profile of the handle cannula 320. This interface between the knob 336 and the handle cannula 320 allows the handle cannula 320 to slide within the channel 336. A length of the handle cannula 320, in this embodiment, is long enough such that the distal tip 323 of the handle cannula 320 is supported by the channel 364 of the trigger assembly 310 at points E and F, as can be seen in the figure, when dimension C is equal to 0. This length of the handle cannula 320 will prevent the knob 336 from being disassembled from the slot 365 of the trigger assembly 310 when the trigger assembly 310 has been positioned within the first actuator 308 via the flex tabs 362. It is noted that in this embodiment, the knob 336 is not glued to the handle cannula 320 because the handle cannula 320 is slidable within the knob channel 366. In this embodiment, the distal tip of the trigger assembly 310 has a lumen 367 through which the distal tip 323 of the handle cannula 320 can be displaced. Referring to FIG. 12 as the first actuator 308 and second actuator 310 are slid in the proximal direction to open the end effector 306, a portion of the lumen 367 will slide proximally over the distal end of the handle cannula 320. In another exemplary embodiment, instead of a lumen, the distal end of the trigger assembly 310 may have a hub that is coupled to the proximal end of the sheath 304. In this embodiment, the hub may be composed of a flexible polymer so that the hub may also be used as a strain relief.

Figure 14:
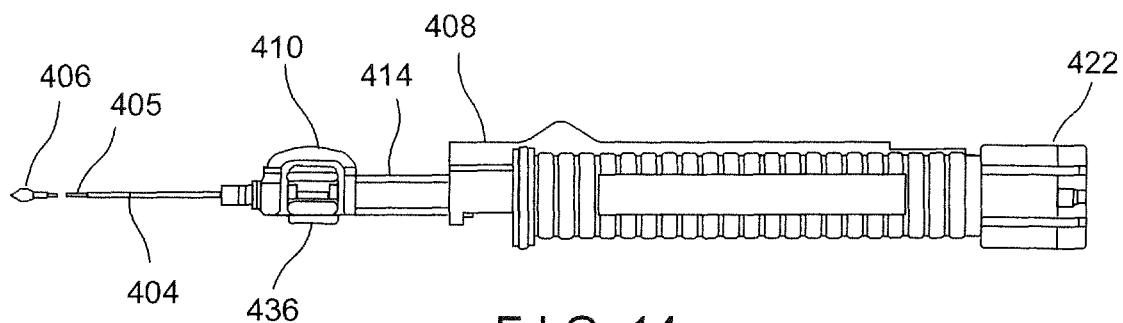
FIG. 14 shows a side view of a retrieval device according to a fifth exemplary embodiment of the present disclosure.

FIGS. 14-18 depict retrieval device designs according to further embodiments of the invention. The retrieval device 400 shown in FIG. 14 are substantially the same as the retrieval device 300 depicted in FIGS. 11-13, except as discussed herein. Regarding FIG. 14, a device 400 is shown with a second actuator 410. However, in this embodiment, the second actuator 410 does not include a trigger. In this embodiment, the knob 436 or the surface of the second actuator 410 may be used instead of the trigger. In an embodiment, the surface of the second actuator 410 or plunger 414 may include ridges or similar characteristics to improve gripability by the user. In this embodiment, the plunger portion 414 of the second actuator 410 may be fixed to the first actuator 408 such that the plunger 414 does not move relative to the first actuator 408. For example, the plunger portion 414 may be glued or molded to the distal end of the first actuator 408. In this embodiment, the device 400 does not include a biasing member because the plunger 414 does not move proximally or distally relative to the first actuator 408. The device 400 still has the single hand operation feature to expand and retract the end effector 406 via the sheath member 404, provide end effector 406 rotation via the knob 436 and provide an electrical current to the end effector 406 via the drive wire 405.

Figure 15:
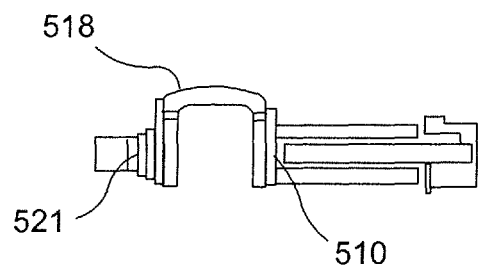
FIG. 15 shows a second actuator of the device of FIG. 11 according to an exemplary embodiment of the present disclosure.

FIG. 15 depicts an exemplary embodiment of a second actuator 510. In this embodiment, the distal portion 518 does not include a trigger, similar to the second actuator 210. The second actuator 510 also has a shorter distal tip 521 extending distally from the knob slot 565 than distal portions 118, 218, 318, 418. In this embodiment, the handle cannula is displaced into the shaft member rather than into the longer distal portions. Thus, this shorter distal tip 521 is preferred when coupling to the LithoVue™ scope for clearance and appearance. However, it will be understood that in some embodiments, the distal tip 521 may be configured so that the handle cannula can be displaced in both the distal tip 521 and the shaft member.

Figure 16:
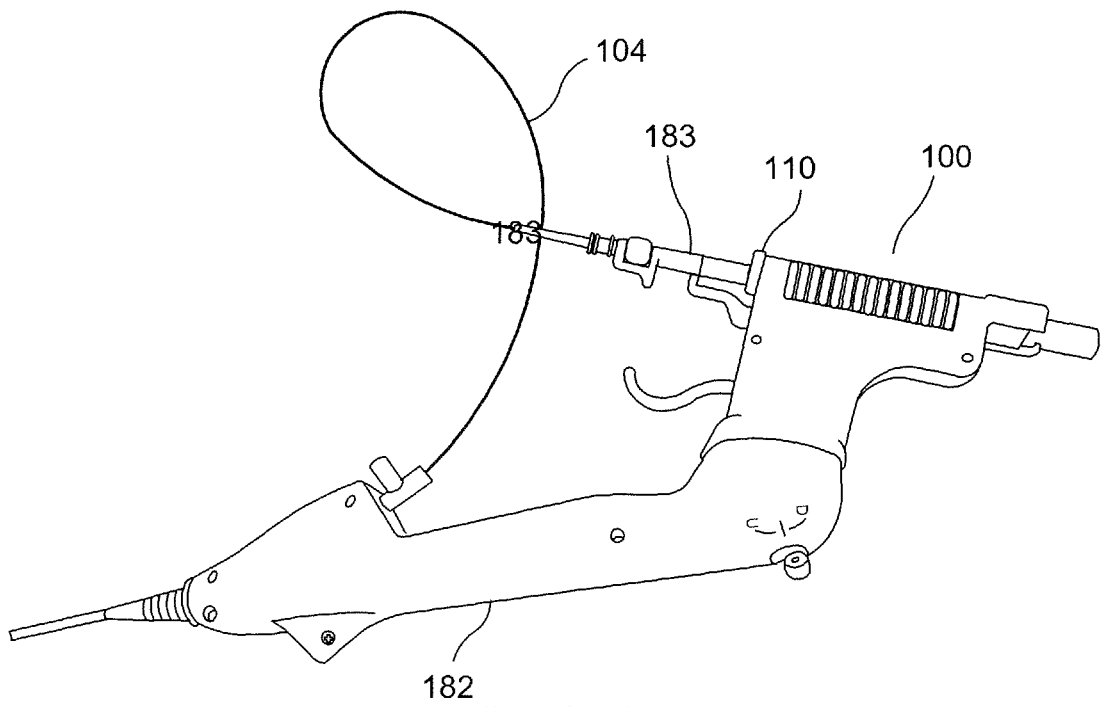
FIG. 16 shows a perspective view of a retrieval device coupled to a LithoVue™ handle.

In an exemplary embodiment depicted in FIG. 16, the device 100 may be used with a LithoVue™ endoscopic device 182. It will be understood that while reference is only made to device 100, any of the previously described devices 200, 300, 400 may also be used. The device 100 is coupled to the LithoVue™ device via an adaptor. In this embodiment, the proximal end of the sheath 104 is connected to a luer hub 183 and the luer hub 183 is connected to the distal end of the second actuator 110.

Figure 18:
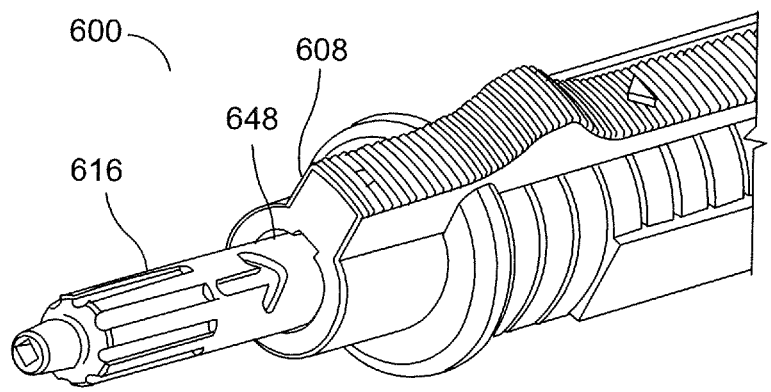
FIG. 18 shows a handle assembly according to an exemplary embodiment of the present disclosure.

In some embodiments, as depicted in FIG. 18, the device 100 may be used with a non-self-expanding end effector such as the Boston Scientific Dakota™ end effector described in U.S. Patent Application 2016/0199079 which is herein incorporated by reference. In this embodiment, a portion of the Dakota™ end effector is attached or associated to both the distal end of the drive wire and the sheath. Therefore, both the drive wire and the sheath are rotated together to prevent torque failure. As depicted in the Figure, the plunger 616 is made with a circular profile such that it can rotate in the distal aperture 648 of the first actuator 608. The plunger 616 also acts as the knob for rotation and is made long enough to displace the distal end of the handle cannula (not shown). The square outer profile of the handle cannula is crimped to the drive wire, as described above, and can slide to engage a square lumen of the plunger 616. Thus, rotation of the plunger 616 rotates the sheath, drive wire and end effector.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

What is claimed is:

1. A handle assembly, comprising:
a drive wire extending from a proximal end to a distal end configured to be coupled to an expandable end effector, the drive wire having a diameter of less than 3 French;
a handle cannula extending from a proximal end to a distal end and configured to receive the drive wire therethrough, the handle cannula including a crimped portion configured to crimp the handle cannula to the drive wire such that rotation of the handle cannula transfers torque to rotate the drive wire, an outer profile of the handle cannula being non-circular in shape;
a shaft member extending from a proximal end to a distal end, the shaft member configured to slidably receive the handle cannula therethrough, an inner profile of the shaft member sized and shaped to match the outer profile of the handle cannula such that rotation of the shaft member transfers torque to rotate the handle cannula, and an outer profile of the shaft member being non-circular in shape; and
an actuation assembly configured to slidably receive the shaft member therein, a distal end of the actuation assembly being coupled to a sheath sized and shaped to receive the drive wire and end effector therethrough, the actuation assembly moveable between a proximal configuration in which the sheath is moved proximally to expand the end effector and a distal configuration in which the sheath is moved distally to retract the end effector, the actuation assembly including a rotation mechanism keyed to the outer profile of the shaft member such that rotation of the rotation mechanism transfers torque to rotate the shaft member,
wherein the actuation assembly includes a first actuation member and a second actuation member, the first actuation member having a lumen separated into a proximal portion and a distal portion via a stop rib, the proximal and distal portions being open to one another via a hole in the stop rib sized and shaped to slidably receive the shaft member therethrough, the distal portion being open to a distal aperture configured to receive a keyed proximal end of the second actuation member.

2. The handle assembly of claim 1, further comprising a locator body extending from a proximal end to a distal end configured to be received within the proximal portion of the first actuation member lumen, the locator body including a lumen sized and shaped to receive the handle cannula, a distal stop for limiting a distal sliding distance of the first actuation member, and a proximal stop limiting a proximal sliding distance of the first actuation member.

3. The handle assembly of claim 1, wherein the second actuation member includes a proximal plunger portion and a distal trigger portion, the plunger portion being keyed to the distal aperture of the first actuation member so as to allow slidable movement of the plunger within the proximal lumen portion of the first actuation mechanism, the trigger portion extending distally from the plunger portion and including a slot to receive the rotation mechanism, the trigger portion configured to be gripped by a user to move the second actuation member proximally and distally relative to the first actuation member to further expand and retract, respectively, the end effector.

4. The handle assembly of claim 3, wherein the rotation mechanism is a knob including a channel extending therethrough sized and shaped to receive the shaft member, an inner profile of the channel keyed to the outer profile of the shaft member.

5. The handle assembly of claim 1, further comprising a biasing member configured to be positioned over a portion of the shaft member within the proximal portion of the first actuation member lumen so as to be compressible between the plunger portion and the stop rib, a restoring force of the biasing member being set to less than a break strength of the end effector so that the sheath is distally movable over the end effector when a target tissue is captured therein.

6. The handle assembly of claim 1, further comprising an end cap with a monopolar plug, the monopolar plug configured to positively complete an energy circuit to the end effector when the actuation assembly is in the proximal configuration.

* * * * *